United States Patent [19]
Rosenberg

[11] Patent Number: 5,797,397
[45] Date of Patent: Aug. 25, 1998

[54] ULTRASOUND IMAGING SYSTEM AND METHOD USING INTENSITY HIGHLIGHTING TO FACILITATE TISSUE DIFFERENTIATION

[75] Inventor: Mark Rosenberg, Mashua, N.H.

[73] Assignee: Hewlett-Packard Company, Palo Alto, Calif.

[21] Appl. No.: 756,298

[22] Filed: Nov. 25, 1996

[51] Int. Cl.$^6$ .................................................. A61B 8/00
[52] U.S. Cl. ......................... 128/660.04; 128/660.07
[58] Field of Search ................. 382/51; 128/660.07, 128/660.04, 660.08, 660.09

[56] References Cited

U.S. PATENT DOCUMENTS

| | | | |
|---|---|---|---|
| 5,042,077 | 8/1991 | Burke | 382/51 |
| 5,322,066 | 6/1994 | Myiataka et al. | 128/660.04 |
| 5,432,871 | 7/1995 | Novik | 382/232 |
| 5,447,153 | 9/1995 | Weil et al. | 128/653.1 X |
| 5,471,989 | 12/1995 | Roundhill et al. | 128/660.04 |
| 5,479,926 | 1/1996 | Ustuner et al. | 128/660.04 |

*Primary Examiner*—Francis Jaworski

[57] ABSTRACT

An ultrasound imaging system generates an ultrasound image that represents ultrasound intensity as a function of position within an object, such as a patient's body. An ultrasound intensity range of interest is selected, and one or more areas of the ultrasound image which represent ultrasound intensities within the selected intensity range are highlighted, typically with a distinctive color. The highlighting of a selected intensity range facilitates analysis of the image and, in particular, facilitates differentiation of tissue types. Highlighting is typically performed within a defined region of interest of the ultrasound image.

15 Claims, 6 Drawing Sheets

ULTRASOUND IMAGING SYSTEM AND METHOD USING INTENSITY HIGHLIGHTING TO FACILITATE TISSUE DIFFERENTIATION

FIELD OF THE INVENTION

This invention relates to ultrasound imaging systems and, more particularly, to ultrasound imaging systems and methods wherein a selected intensity range is highlighted in the ultrasound image to facilitate image analysis.

BACKGROUND OF THE INVENTION

Ultrasound imaging is widely used in medial applications to noninvasively observe structures within the human body, such as, for example, cardiac structures, the vascular system, the fetus, the uterus, the abdominal organs and the eye. In a typical imaging system, short bursts of ultrasound energy are directed into a patient's body with a handheld transducer. The returning reflected ultrasound energy, or echos, are received by the same transducer and are converted to electrical signals. The signals representing the reflected energy are processed and formatted into a video image of a target region. In an imaging mode commonly known as B-mode imaging, the ultrasound image is a two-dimensional image which represents reflected ultrasound intensity as a function of position within the target region of the patient's body. The ultrasound image may be generated using well-known phased array ultrasound scanning techniques. Scanning formats include sector scanning, linear scanning and curved linear scanning. In each case, scanning signals representative of received intensity and the corresponding position information are converted into a conventional raster scan display. Each pixel in the raster scan display has a pixel value that represents reflected ultrasound intensity at a given position within the target region. In the image, the pixel value is represented by a gray scale value between white and black.

A typical ultrasound image may utilize 8-bit pixel values, which represent 256 gray scale values. However, the human eye is unable to distinguish this many gray scale values. Accordingly, it may be difficult or impossible to discern certain features or to differentiate between certain tissue types in a conventional monochrome ultrasound image. It is therefore desirable to provide enhancements which permit the user of the ultrasound imaging system to gain additional useful information from the ultrasound image.

Color flow ultrasound images show velocities, such as blood velocities, within the field of view. One prior art system utilizes a color tag feature that provides the user with the capability to assign a unique discriminating color to a single velocity or a range of velocities within the displayed color flow image. Velocities within the selected range are represented in the image by the discriminating color. The user is able to distinguish selected velocity range in the discriminating color and to identify peak velocities that may not be visually apparent to the eye in the absence of the discriminating color because of the limited dynamic range of colors in the image.

SUMMARY OF THE INVENTION

According to a first aspect of the invention, a method for displaying an ultrasound image in an ultrasound imaging system is provided. The method comprises the steps of generating an ultrasound image that represents ultrasound intensity as a function of position within an object, such as a patient's body, selecting an ultrasound intensity range of interest and highlighting one or more areas of the ultrasound image which represent ultrasound intensities within the selected intensity range. Preferably, a region of interest is defined within the ultrasound image, and highlighting is limited to the region of interest. The highlighted areas facilitate visual analysis of the ultrasound image and, in particular, may facilitate differentiation between tissue types in the image.

Preferably, areas of the ultrasound image which represent intensities within the selected intensity range are highlighted with a color that is easily distinguishable from non-highlighted areas of the ultrasound image. A scale that represents possible shades in the ultrasound image may be displayed adjacent to the image. In one approach, a range of shades corresponding to the selected intensity range is selected using the scale. In another approach, a feature of interest in the ultrasound image is selected with a pointing device, and the ultrasound intensity range of interest is defined as including the ultrasound intensity of the selected feature of interest.

According to another aspect of the invention, an ultrasound imaging system is provided. The imaging system comprises an image generating apparatus for generating an ultrasound image that represents ultrasound intensity as a function of position within an object, means for selecting an ultrasound intensity range of interest and means for highlighting one or more areas of the ultrasound image which represent ultrasound intensities within the selected intensity range.

Preferably, the means for highlighting includes a transformation memory, having a memory location for each possible pixel value in the ultrasound image, and a color lookup table addressed by an output of the transformation memory. Memory locations in the transformation memory associated with pixel values within the selected intensity range contain a highlight code, and memory locations in the transformation memory associated with pixel values outside the selected intensity range contain corresponding pixel values. The transformation memory is addressed by successive pixel values of the ultrasound image during generation of the ultrasound image. The transformation memory outputs the highlight code when the pixel value is within the selected intensity range and outputs a corresponding pixel value when the pixel value is outside the selected intensity range. The transformation memory may include a first section containing only corresponding pixel values and a second section containing the highlight code in memory locations associated with pixel values within the selected intensity range. The second section of the transformation memory is addressed when the pixel being addressed is within a region of interest of the ultrasound image. The first section of the transformation memory is addressed when the pixel being addressed is outside the region of interest.

BRIEF DESCRIPTION OF THE DRAWINGS

For a better understanding of the present invention, reference is made to the accompanying drawings, which are incorporated herein by reference and in which.

DETAILED DESCRIPTION

The present invention provides methods and apparatus for facilitating visual analysis of ultrasound images generated by an ultrasound imaging system. A range of ultrasound intensities is selected as being of interest, generally because a structure may exhibit intensities that are within a range different from the surrounding tissue. One or more areas of the ultrasound image which represent intensities within the selected ultrasound intensity range are highlighted in the ultrasound image, typically by a distinctive color. With the ability to highlight selected intensity ranges, the user may, for example, be able to identify diffuse infiltrative processes that exhibit unique tissue density patterns that differ from the surrounding tissue. These processes include, for example, rare cancers, infections and infarcts. The invention is useful, for example, in situations where boundaries and contours of suspect areas in the image are imperceptible or barely perceptible to the eye and the user wishes to enhance those areas for inspection.

Figure 1:
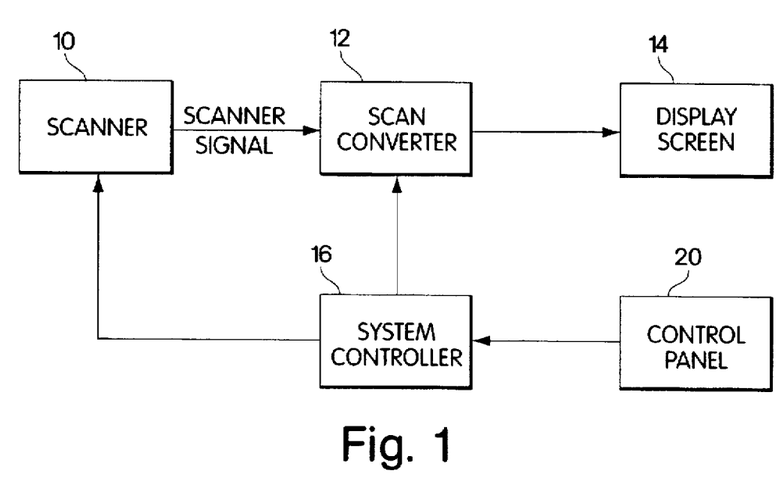
FIG. 1 is a block diagram of an example of an ultrasound imaging system suitable for incorporation of the present invention.

A simplified block diagram of an ultrasound imaging system suitable for incorporation of the present invention is shown in FIG. 1. A scanner 10 performs ultrasound scanning of a target region of a patient's body. The scanner 10 includes an ultrasound transducer for transmitting and receiving ultrasound energy. The transducer transmits ultrasound energy into a region being imaged and receives reflected ultrasound energy from various structures, tissues and organs within the patient's body.

The transducer may include an array of transducer elements. As known in the prior art, by appropriately delaying the pulses applied to each transducer element, a focused ultrasound beam is transmitted along a desired scan line. Reflected ultrasound energy from a given point within the patient's body is received by the transducer elements at different times. The transducer elements convert the received ultrasound energy to electrical signals which are supplied to a receive beamformer. The delayed signals from each transducer element are summed by the beamformer to provide a scanner signal that represents the reflected energy level along a given scan line. The process is repeated for multiple scan lines to provide signals for generating an image of the target region of the patient's body. The scan pattern may be a sector scan, wherein scan lines originate at the center of the ultrasound transducer and are directed at different angles. A linear, curvilinear or any other scan pattern can also be utilized.

The scanner signal is applied to a scan converter 12, which converts the sector scan information generated by scanner 10 to a conventional raster scan display signal. The output of scan converter 12 is applied to a video display screen 14, which displays an image of the target region of the patient's body. A system controller 16 provides overall control of the system. The system controller 16 performs timing and control functions and may include a microprocessor and associated memory. A control panel 20 permits user control of the system. The control panel 20 may, for example, include a conventional alphanumeric keyboard, dedicated function keys, a trackball, one or more touch panels and various adjustment controls. The trackball permits control of the position of a cursor on the display screen 14 in operating modes where a cursor is utilized. An example of an ultrasound imaging system suitable for incorporation of the present invention is the Sonos 2000, manufactured and sold by Hewlett-Packard Company.

Figure 2:
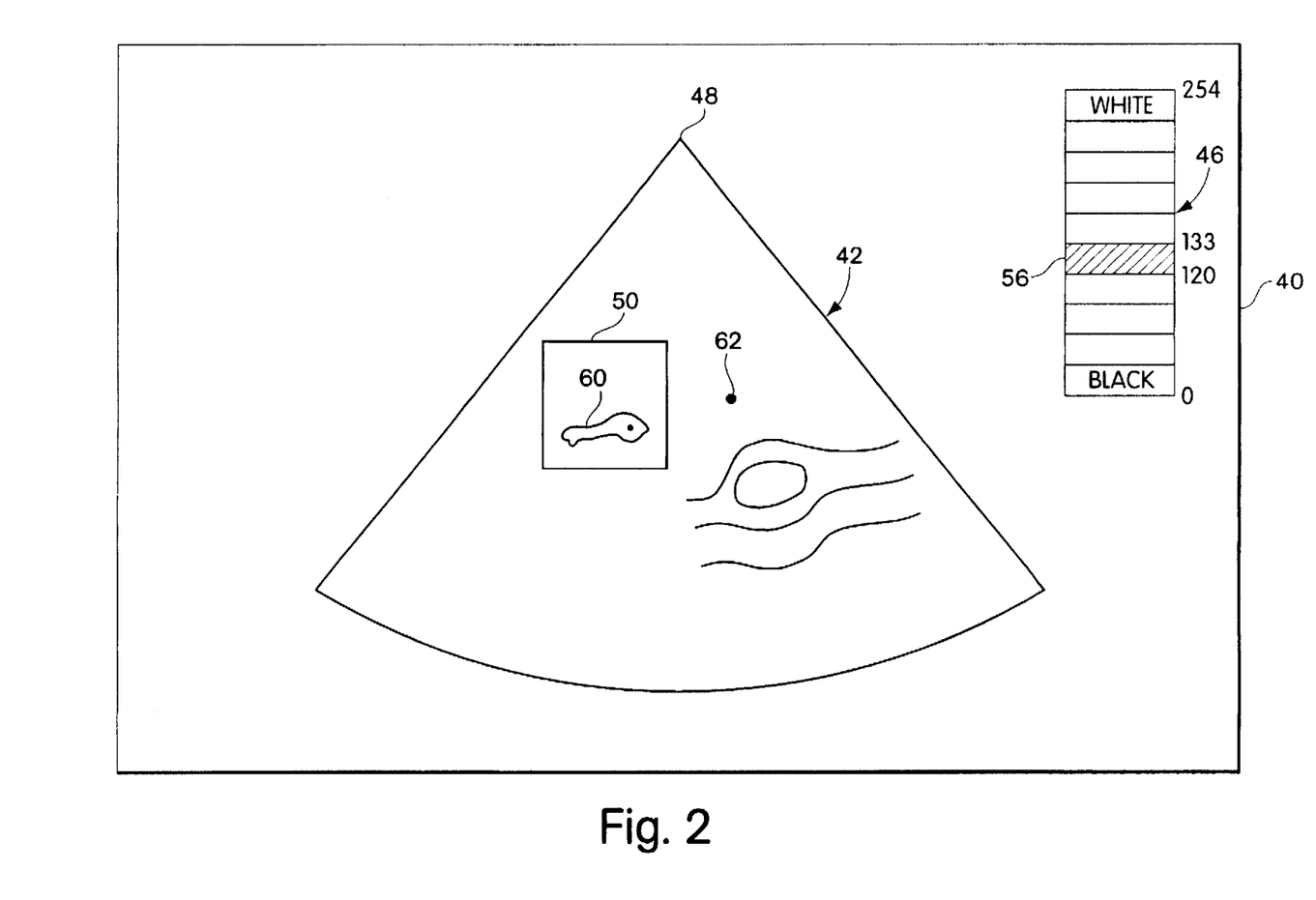
FIG. 2 illustrates an example of an ultrasound image having intensity highlighting in accordance with the invention.

A simplified ultrasound image display is illustrated in FIG. 2. An image display 40, which may appear on display screen 14, includes a sector scan ultrasound image 42 and a gray bar 46. The image 42 within a sector-shaped area represents received ultrasound intensity as a function of angle and depth from an apex 48 of the scan pattern. The image display 40 is generated using conventional raster scan display techniques. Thus, ultrasound image 42 is represented by rows and columns of pixels, each having a digital pixel value representative of ultrasound intensity. The imaging system may permit a region of interest (ROI) 50 to be defined. The ROI 50 is typically indicated on the display by a line, such as a square or rectangle, that surrounds the region of interest. The imaging system may permit the user to vary the size of ROI 50 and to change its position relative to image 42.

A gray bar 46 may be positioned on the display screen adjacent to image 42. The gray bar 46 is a scale of possible discrete shades in the ultrasound image. The gray bar 46 indicates shades, corresponding to the possible pixel values, ranging from white to black and may be used as described below in selecting an ultrasound intensity range for highlighting. Corresponding pixel values may be displayed next to the gray bar 46.

In accordance with the invention, an ultrasound intensity range of interest is selected by the user in a tissue differentiation mode. The selected intensity range may correspond to a range of gray shades on the image. Thus, the intensity range of interest may be selected by selecting a gray scale range, such as gray scale range 56. The range 56 may, for example, be selected at the control panel 20 using the touch panel and one or more designated adjustment knobs. In particular, the user selects a tissue differentiation mode and then selects an ultrasound intensity range of interest. Both the span and the starting intensity of the range may be selected. The range may be large or small and may be moved anywhere on gray bar 46. Any convenient technique may be utilized for selecting the intensity range of interest. For example, the intensity range may be selected by one or more adjustment knobs, by an alphanumeric keyboard, by control keys which increment the starting intensity and the span, with the trackball and appropriate menu selections, or by any other suitable selection technique.

Ultrasound intensities are typically represented in the imaging system by discrete digital pixel values. A typical system may utilize 8-bit pixel values, thus providing the ability to differentiate up to 256 intensities. The pixel values are converted to different gray shades in the ultrasound image. Alternatively, ultrasound intensities may be represented by analog signals. In each case, the phrase "intensity range" as used herein may encompass a single intensity value or a number of intensity values.

After the ultrasound intensity range of interest is selected, all pixels located within ROI 50 and having pixel values within range 56 are highlighted. The highlighting typically uses a distinctive color. However, any highlighting technique which clearly indicates areas of image 42 representing ultrasound intensity values within the selected intensity range may be utilized. Thus, for example, an area 60 within ROI 50 having pixel values in the range of 120 to 133 (corresponding to selected range 56) is highlighted. A pixel 62 located outside ROI 50 is not highlighted, even when its pixel value falls within the selected intensity range. It will be understood that the ROI 50 is an optional feature which permits the user to focus on a particular region of the image 42. However, highlighting of a selected intensity range may be performed on the entire ultrasound image 42 within the scope of the present invention. It will further be understood that areas including single pixels, contiguous groups of pixels and spaced-apart groups of pixels may be highlighted, depending on the pixel value of each pixel.

The tissue differentiation mode may optionally provide the ability to turn highlighting of a selected intensity range on and off. The highlighting may be toggled on and off. For example, using a key on the touch panel of the control panel 20. This feature permits the user to suppress highlighting and to observe the underlying tissue in the ultrasound image without highlighting.

Figure 3:
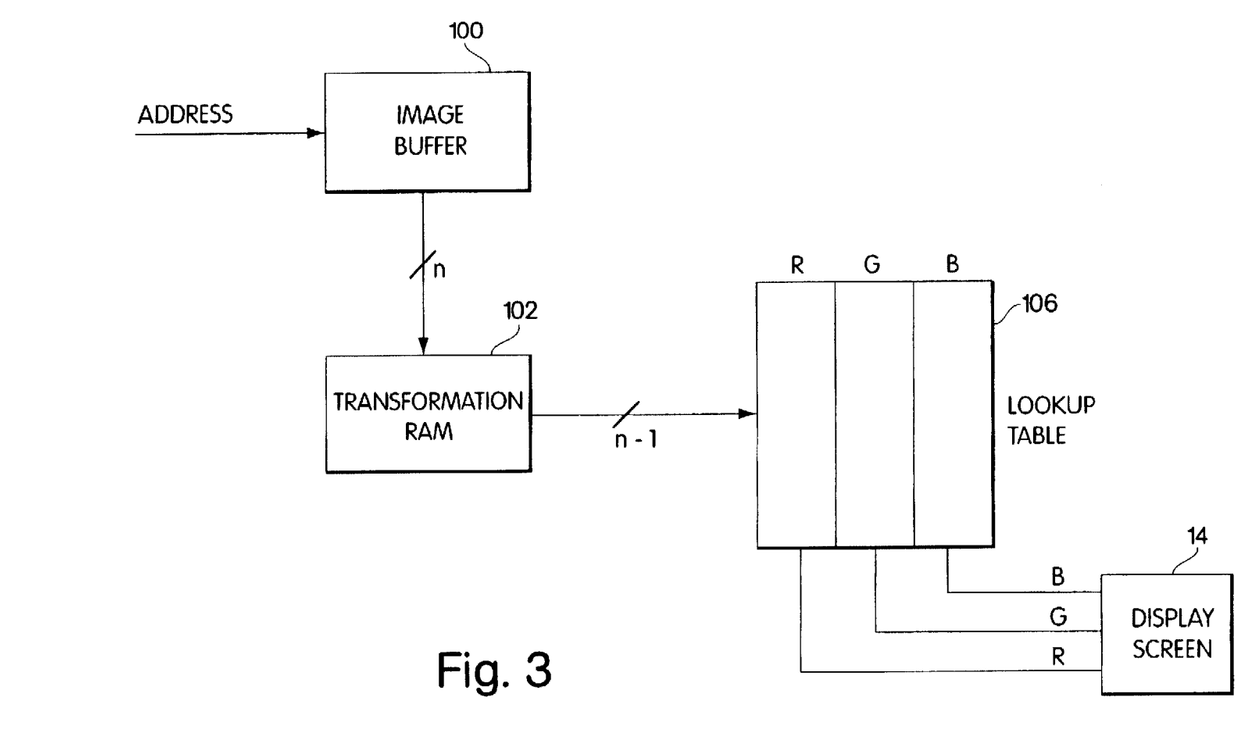
FIG. 3 is a block diagram of a portion of the ultrasound imaging system showing an example of elements that may be used to implement highlighting in accordance with the invention.

A block diagram of elements of one implementation of the scan converter 12, which may be utilized to generate an ultrasound image having highlighting of a selected intensity range, is shown in FIG. 3. An image buffer 100 contains n bits for each pixel in the ultrasound image. A typical image may include 150,000 pixels. An address input to image buffer 100 selects a pixel location. Each pixel location includes a pixel value of n−1 bits and an ROI bit. Thus, for example, each pixel location may include an 8 bit pixel value and a single ROI bit, for a total of 9 bits. One code of the n 1 bits may be reserved for a highlight code as described below. Thus, where the pixel value has 8 bits, there are 255 possible pixel values. The ROI bit indicates whether the pixel is inside or outside region of interest 50. The data outputs of image buffer 100, comprising the n bits of an addressed pixel location, are supplied to a transformation memory, or transformation RAM 102. As described below, the transformation RAM 102 outputs n- 1 bits to a color lookup table 106. When the pixel being processed is located within region of interest 50 and the pixel value is within the selected intensity range, the transformation RAM 102 outputs a highlight code to lookup table 106. Otherwise, the transformation RAM 102 outputs the pixel value to lookup table 106. The lookup table 106 contains a series of red, green and blue color values for activating a pixel on display screen 14. For unhighlighted pixels, a gray scale value corresponding to the pixel value is addressed in table 106. For highlighted pixels, a highlight color defined by the highlight code is addressed. The addressed color values are output by lookup table 106 to display screen 14 for generation of the ultrasound image.

Figure 4:
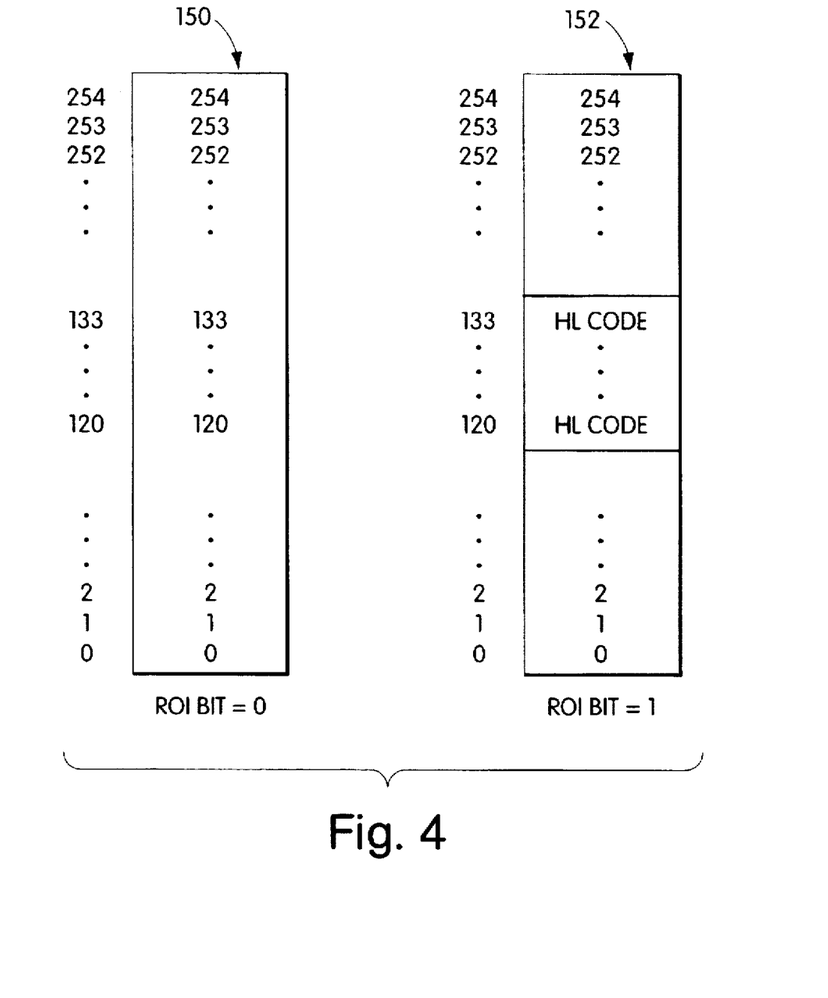
FIG. 4 illustrates an example of the organization of the transformation RAM shown in FIG. 3.

Referring now to FIG. 4, an example of the organization of transformation RAM 102 is illustrated. In the illustrated example, an 8-bit pixel value is utilized. The transformation RAM 102 includes a first section 150 and a second section 152. The first and second sections 150 and 152 are addressed by pixel values output from image buffer 100. The first section 150 is accessed when the ROI bit is not set (ROI bit=0) and includes one location for each possible pixel value. Thus, for an 8-bit pixel value, with one code reserved for a highlight code, the first section 150 includes 255 locations. The 255 locations contain each of the possible pixel values 0 to 254. The second section 152 is accessed when the ROI bit is set (ROI bit=1) and also contains 255 locations for an 8-bit pixel value. In the second section 152, the memory locations contain pixel values 0 to 254, except for memory locations addressed by pixel values within the selected intensity range. In the example of FIG. 4, an intensity range corresponding to pixel values in a range of 120 to 133 has been selected. The locations in the second section 152 corresponding to pixel values in the range of 120 to 133 contain a unique highlight code.

As indicated above, the output of image buffer 100 is used as an address for the transformation RAM 102. When the image buffer 100 outputs a pixel value with the ROI bit not set, the first section 150 is addressed and the pixel value is output by transformation RAM 102. When the ROI bit is set, the second section 152 of transformation RAM 102 is addressed. When the pixel value is outside the selected intensity range, the pixel value is output to lookup table 106. When the pixel value is within the selected intensity range, the highlight code is output to lookup table 106. Thus, the transformation RAM 102, in effect, passes the pixel value from image buffer 100 to lookup table 106, except when the ROI bit is set and the pixel value is within the selected intensity range. In that case, the transformation RAM 102 provides the highlight code to lookup table 106.

Figure 5:
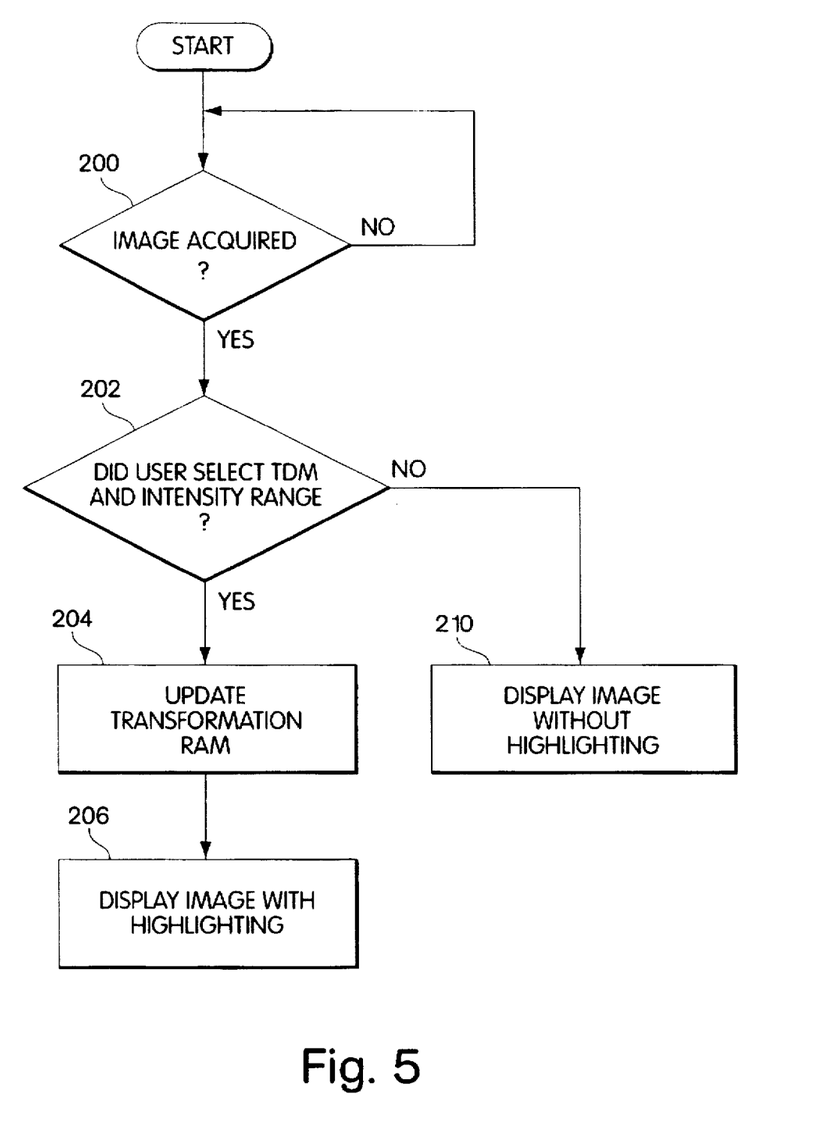
FIG. 5 is a flow diagram of an example of a process for displaying an ultrasound image in accordance with the invention.
Figure 6:
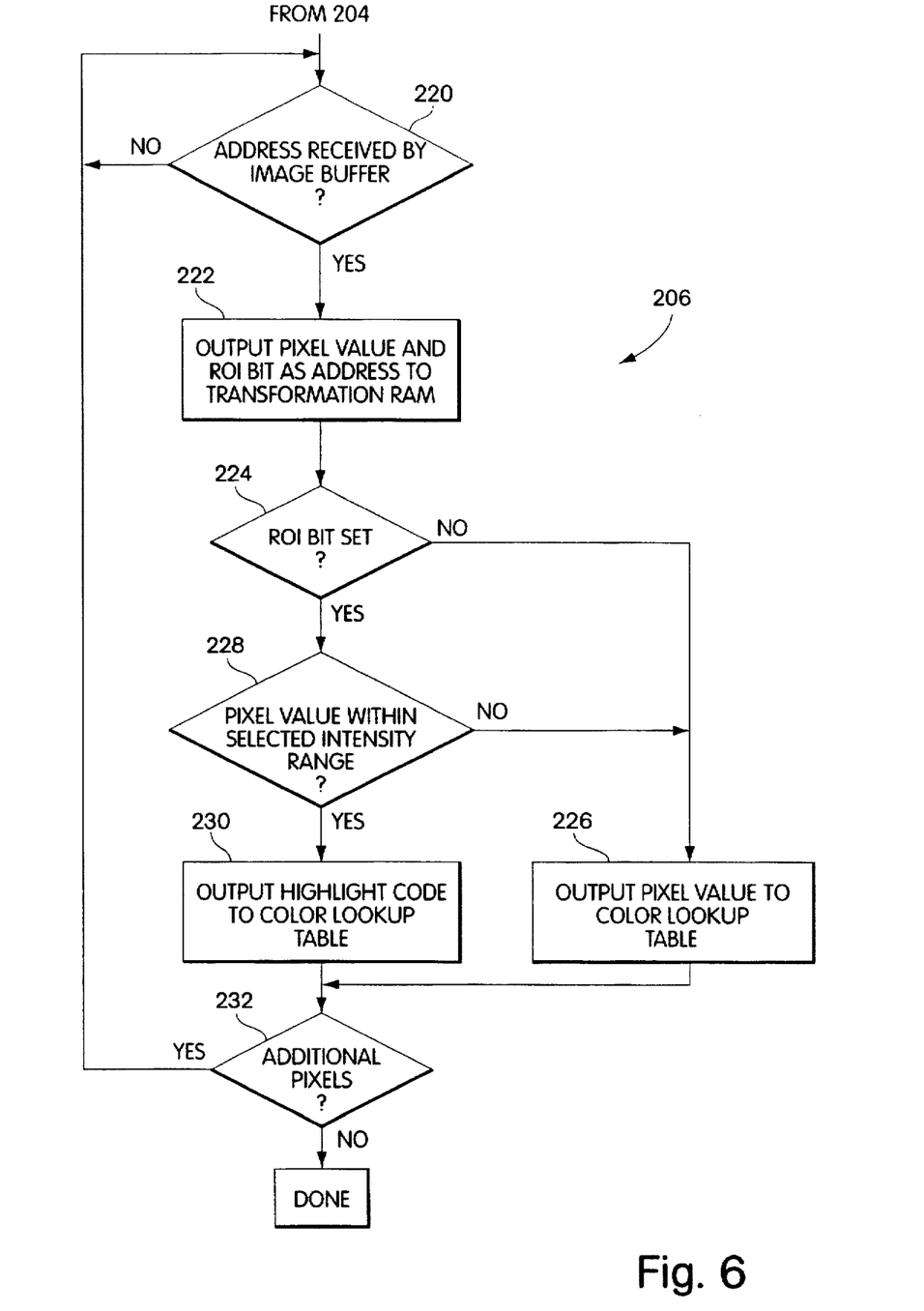
FIG. 6 is a flow diagram of an example of a process for displaying an ultrasound image with intensity highlighting in accordance with the present invention.

Operation of the ultrasound imaging to implement highlighting of a selected intensity range is illustrated in the flow charts of FIGS. 5 and 6. When it is determined in step 200 that an image has been acquired and it is determined in step 202 that the user selected the tissue differentiation mode and a corresponding intensity range, the transformation RAM is updated in step 204. In particular, the highlight code is loaded into those locations in the second section 152 of transformation RAM 102 that correspond to the selected intensity range. With reference to FIG. 4, when the selected intensity range corresponds to pixels having values in the range of 120 to 133, the highlight code is loaded into the corresponding locations of transformation RAM 102. The image may then be displayed by highlighting pixels in the selected intensity range in step 206. When the user does not select the tissue differentiation mode and an intensity range in step 202, the image is displayed without highlighting in step 210.

The details of display step 206 of FIG. 5 are shown in FIG. 6. The pixel locations in image buffer 100 are addressed sequentially to generate an ultrasound image. When an address is received by image buffer 100 in step 220, a pixel value and an ROI bit are output by image buffer 100 to transformation RAM 102 in step 222. The pixel value and the ROI bit address the transformation RAM 102 as illustrated in FIG. 4. When it is determined in step 224 that the ROI bit is not set, the first section 150 of transformation RAM 102 is accessed, and the corresponding pixel value is output to color lookup table 106 in step 226. When it is determined in step 224 that the ROI bit is set, the second section 152 of transformation RAM 102 is accessed. A determination is made in step 228 whether the pixel value is within the selected intensity range. When the pixel value is not within the selected intensity range, the corresponding pixel value is output to color lookup table 106 in step 226. When the ROI bit is set and the pixel value is within the selected intensity range, the highlight code is output to color lookup table 106 in step 230. The highlight code addresses a distinctive color value in lookup table 106. The color value is output by lookup table 106 on R, G, and B lines and causes the pixel to be highlighted on display screen 14. A determination is made in step 232 whether additional pixels require processing. When additional pixels require processing, the process returns to step 220 for receiving the next pixel address. The process is repeated for each pixel in the ultrasound image.

A particular implementation for highlighting a selected intensity range is described in connection with FIGS. 3 and 4. It will be understood that different implementations of highlighting may be utilized. For example, digital comparators may be utilized to determine whether each pixel value is within the selected intensity range and whether each pixel address is within a range corresponding to the dimensions and location of the region of interest. Furthermore, the invention is not limited to digital implementations. In an analog display system, conventional signal processing techniques may be utilized to determine whether the analog intensity signal is within a selected intensity range. Additionally, the intensity range of interest is not necessarily selected utilizing a gray bar as shown in FIG. 2. For example, the trackball or other pointing device of the ultrasound imaging system may be used to position the cursor on a feature of interest in the ultrasound image. When the pointing device is clicked on the feature of interest, an intensity range is established. The selected intensity range includes the pixel value of the pixel on which the cursor was positioned in the feature of interest. Alternatively, the selected intensity range may be determined by averaging several pixels in the region where the cursor was positioned or by some other processing of the pixel values. The span of the intensity range in this embodiment may be a default value or a span which is selectable by the user. For example, the selected intensity range may be defined as including a prescribed number of pixel values on either side of the selected pixel value. This approach permits the user to highlight a particular feature of interest in the ultrasound image, without knowing the ultrasound intensity of the feature of interest. As indicated above, highlighting within a user selected region of interest or a default region of interest is optional. The highlighting may be performed on the entire ultrasound image within the scope of the present invention. As an alternative to the configuration of FIG. 3, transformation RAM 102 and the lookup table 106 may be combined in a single lookup table having a first section that is addressed when the ROI bit is reset in a second section that is addressed when the ROI bit is set. The combined lookup table is addressed by the pixel value and the ROI bit output by the image buffer 100.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for displaying an ultrasound image in an ultrasound imaging system, comprising the steps of:

generating an ultrasound image that represents ultrasound intensity as a function of position within an object;

selecting an ultrasound intensity range of interest; and highlighting one or more areas of the ultrasound image which represent ultrasound intensities within the selected intensity range, said ultrasound imaging system including a video display screen for displaying said ultrasound image and a pointing device, the step of selecting an ultrasound intensity range of interest including selecting a feature of interest in said ultrasound image with said pointing device and defining said ultrasound intensity range of interest as including the ultrasound intensity of the selected feature of interest.

2. A method as defined in claim 1 wherein the step of highlighting one or more areas of the ultrasound image includes displaying said one or more areas of the ultrasound image in a color that is easily distinguishable from non-highlighted areas of the ultrasound image.

3. A method as defined in claim 1 further including the step of defining a region of interest in said ultrasound image and wherein the step of highlighting one or more areas of the ultrasound image includes highlighting only the one or more areas of the ultrasound image that are within said region of interest.

4. A method as defined in claim 1 further including the step of examining the highlighted one or more areas of the ultrasound image to differentiate between tissue types in the ultrasound image.

5. An ultrasound imaging system comprising:

image generating apparatus for generating an ultrasound image that represents ultrasound intensity as a function of position within an object;

means for selecting an ultrasound intensity range of interest; and means for highlighting one or more areas of the ultrasound image which represent ultrasound intensities within the selected intensity range, said means for highlighting including a transformation memory having a memory location for each possible pixel value in said ultrasound image and a color lookup table addressed by an output of said transformation memory, wherein memory locations in said transformation memory associated with pixel values within said selected intensity range contain a highlight code and memory locations in said transformation memory associated with pixel values outside said selected intensity range contain corresponding pixel values, wherein said transformation memory is addressed by successive pixel values of the ultrasound image during generation of the ultrasound image, wherein said transformation memory outputs the highlight code when the pixel value is within the selected intensity range and outputs a corresponding pixel value when the pixel value is outside the selected intensity range.

6. An ultrasound imaging system as defined in claim 5 wherein said means for highlighting includes means for displaying one or more areas of the ultrasound image which represent ultrasound intensities within the selected intensity range in a color that is easily distinguishable from non-highlighted areas of said ultrasound image.

7. An ultrasound imaging system as defined in claim 5 wherein said image generating apparatus includes means for generating adjacent to said ultrasound image a scale that represents a range of shades in said ultrasound image and wherein said means for selecting an ultrasound intensity range of interest includes means for selecting a range of shades from said scale.

8. An ultrasound imaging system as defined in claim 5 further including means for defining a region of interest in said ultrasound image and wherein said means for highlighting includes means for highlighting only the one or more areas of the ultrasound image that are within said region of interest.

9. An ultrasound imaging system as defined in claim 5 wherein said image generating apparatus comprises a scanner for ultrasound scanning of a target region of a patient's body and for generating a scanner signal representative of ultrasound energy reflected from the target region, an image generator responsive to the scanner signal for generating said ultrasound image of the target region, a video display screen for displaying said ultrasound image, a control unit for controlling said scanner and said image generator during scanning and generation of said ultrasound image, and a control panel for operator control of said ultrasound imaging system.

10. An ultrasound imaging system as defined in claim 9 wherein said control panel includes a pointing device and wherein said means for selecting an ultrasound intensity range of interest includes means responsive to selection of a feature of interest in said ultrasound image with said pointing device for defining said ultrasound intensity range of interest as including the ultrasound intensity of the selected feature of interest.

11. An ultrasound imaging system as defined in claim 5 wherein said transformation memory includes a first section containing only corresponding pixel values and a second section containing said highlight code in memory locations associated with pixel values within the selected intensity range, wherein the second section of said transformation memory is addressed when the pixel being displayed is within a region of interest of said ultrasound image and wherein the first section of said transformation memory is addressed when the pixel being displayed is outside said region of interest.

12. A method as defined in claim 1 wherein the step of generating an ultrasound image includes generating an image that represents a two-dimensional space in the target region of the patient's body.

13. A method as defined in claim 1 wherein the step of generating an ultrasound image includes generating an image that represents a three-dimensional volume in the target region of the patient's body.

14. Apparatus for generating an ultrasound image, comprising:

an image buffer for storing pixel values of an ultrasound image that represents ultrasound intensity as a function of position within an object;

a transformation memory responsive to pixel values output by said image buffer, said transformation memory including a memory location for each possible pixel value in said ultrasound image, memory locations in said transformation memory associated with pixel values within a selected intensity range containing a highlight code and memory locations in said transformation memory associated with pixel values outside the selected intensity range containing corresponding pixel values; and a color lookup table addressed by an output of said transformation memory for supplying color values to a video display screen, wherein said transformation memory is addressed by successive pixel values from the image buffer during generation of the ultrasound image, wherein said transformation memory outputs the highlight code when the pixel value is within the selected intensity range and outputs a corresponding pixel value when the pixel value is outside the selected intensity range, wherein one or more areas of the ultrasound image which represent ultrasound intensities within the selected intensity range are highlighted.

15. An ultrasound imaging system comprising:

image generating apparatus for generating an ultrasound image that represents ultrasound intensity as a function of position within an object, said image generating apparatus comprising a scanner for ultrasound scanning of a target region of a patient's body and for generating a scanner signal representative of ultrasound energy reflected from the target region, an image generator responsive to the scanner signal for generating said ultrasound image of the target region, a video display screen for displaying said ultrasound image, a control unit for controlling said scanner and said image generator during scanning and generation of said ultrasound image, and a control panel for operator control of said ultrasound imaging system, said control panel including a pointing device;

means for selecting an ultrasound intensity range of interest, including means responsive to selection of a feature of interest in said ultrasound image with said pointing device for defining said ultrasound intensity range of interest as including the ultrasound intensity of the selected feature of interest; and means for highlighting one or more areas of the ultrasound image which represent ultrasound intensities within the selected intensity range.

\* \* \* \* \*